United States Patent [19]

Schultz, Jr. et al.

[11] 4,352,163
[45] Sep. 28, 1982

[54] VECTORCARDIOGRAM SIMULATOR

[75] Inventors: Edward R. Schultz, Jr.; Kenneth J. Cook, both of Troy; Joseph S. Power, Fraser; Frederick B. Ruszala, Sterling Heights, all of Mich.

[73] Assignee: The Valeron Corporation, Troy, Mich.

[21] Appl. No.: 93,085

[22] Filed: Nov. 9, 1979

[51] Int. Cl.³ .............................................. G06G 7/48
[52] U.S. Cl. .................................... 364/801; 128/668; 364/417; 364/578
[58] Field of Search ................ 364/578, 801, 415–417, 364/487, 521; 128/668, 695, 672, 699, 702

[56] References Cited

U.S. PATENT DOCUMENTS

| | | | |
|---|---|---|---|
| 3,267,934 | 8/1966 | Thornton | 128/702 |
| 3,323,068 | 5/1967 | Woods | 328/187 |
| 3,384,981 | 5/1968 | Baessler et al. | 35/17 |
| 3,548,813 | 12/1970 | Berner | 364/417 |
| 3,552,036 | 1/1971 | Mahler | 35/17 |
| 3,736,363 | 5/1973 | Baessler et al. | 35/17 |
| 3,811,040 | 5/1974 | Weinfurt et al. | 364/415 |
| 3,938,051 | 2/1976 | Eisenberg | 328/187 |
| 4,205,386 | 5/1980 | Ruszala et al. | 364/578 |

Primary Examiner—Errol A. Krass
Attorney, Agent, or Firm—Krass, Young & Schivley

[57] ABSTRACT

A method and apparatus are disclosed for generating simulated waveforms for testing the operability of a vectorcardiogram (VCG) machine. Three distinct waveforms are provided which generally simulate electrical activity within the human heart along three separate axes. Preferably, the waveforms are generated from a single electrocardiographic reference signal. The apparatus includes a plurality of connectors which are selectively coupled to the waveforms and supply output signals to the VCG machine which correspond to waveforms which would ordinarily be supplied by a plurality of electrodes attached to a live patient at various positions.

22 Claims, 8 Drawing Figures

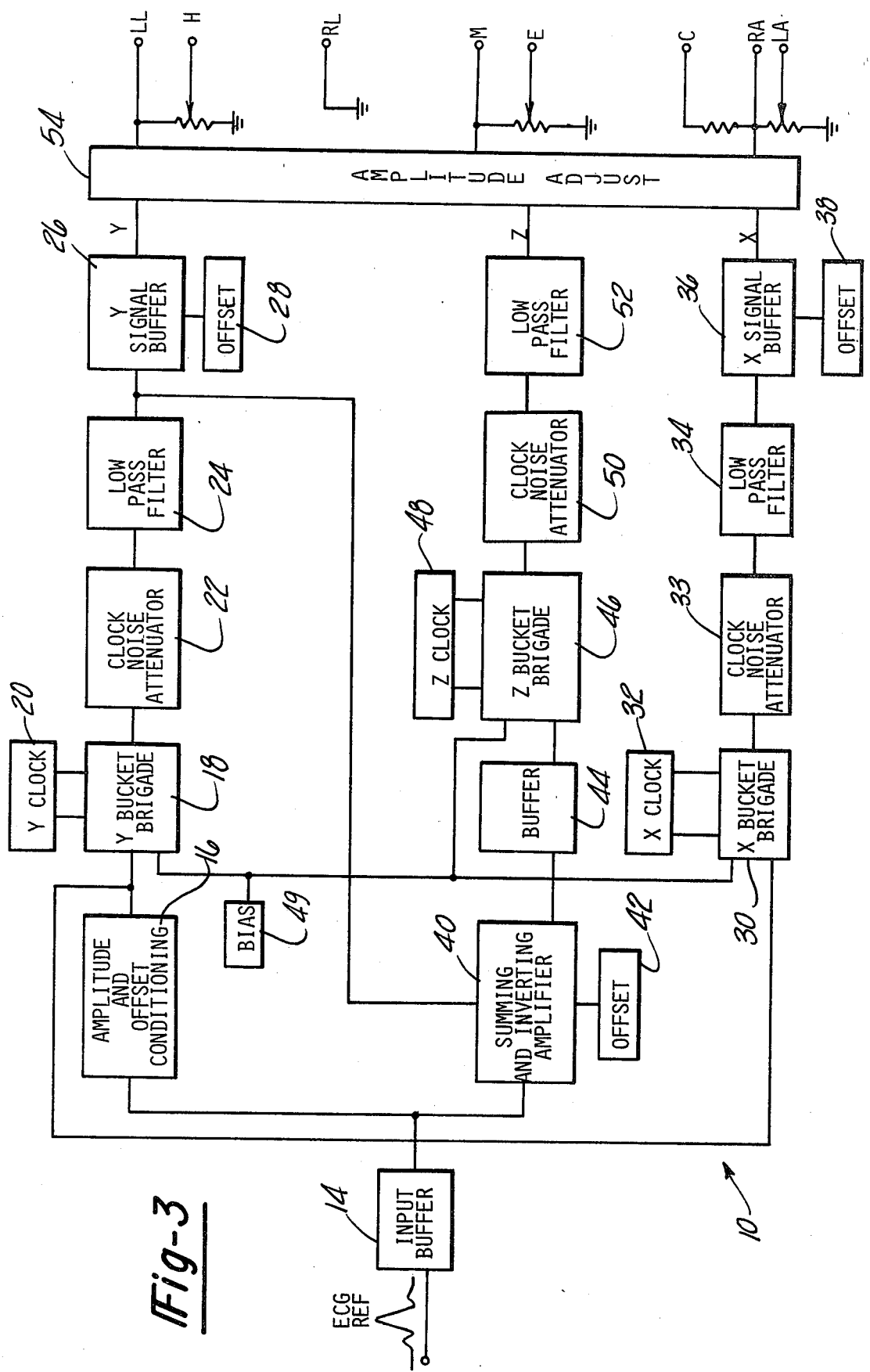

VECTORCARDIOGRAM SIMULATOR

CROSS REFERENCE TO RELATED APPLICATIONS

This application is related to co-pending application entitled "Interconnection System For A Biological Waveform Simulator Device" by Power et al, U.S. Ser. No. 93,086, now U.S. Pat. No. 4,267,576, filed concurrently herewith and having the same assignee as the present invention.

BACKGROUND OF THE INVENTION

This invention relates to waveform generators and, more particularly, to biological waveform simulator devices for testing the operability of medical electronic equipment.

There is an increasing trend towards using more electronic equipment in the medical profession. Typical of such equipment includes the use of blood pressure monitors, electrocardiogram machines, and vectorcardiogram machines. It is obviously of paramount importance that these devices operate properly at all times. For many years, malfunctions of these devices were detected primarily by observing the operation of the machine on a live patient. The time required to either fix the malfunction or replace the machine is obviously detrimental in emergency situations. Moreover, it was difficult to detect whether the machine, while appearing to perform normally, was actually calibrated properly and generating a correct reading.

To correct many of these problems noted above, simulator devices have been utilized to simulate biological waveforms that can be used to test the operability of blood pressure monitors and electrocardiogram machines. Examples of these devices are more fully disclosed in U.S. Ser. No. 882,357, entitled "Complex Analog Signal Generator", filed Mar. 1, 1978, (now U.S. Pat. No. 4,204,261); and U.S. Ser. No. 938,430, entitled "Electrocardiographic Blood Pressure Waveform Simulator Device", filed Aug. 31, 1978, (now U.S. Pat. No. 4,205,386). These simulators, while having provided extremely satisfactory results, are not capable of testing the operability of a vectorcardiogram machine. Vectorcardiogram machines are somewhat complicated devices in which electrocardiograms are taken along three axes (X, Y, and Z) at right angles to one another, with any two of these ECG's being displayed as a vector on an X-Y oscilloscope. The present invention is directed to fulfilling a long felt need for a reliable, yet relatively inexpensive, means for testing the operability of vectorcardiogram machines before being utilized on a live patient.

SUMMARY OF THE INVENTION

This need has been accomplished by way of an electronic waveform simulator device made in accordance with this invention which simulates waveforms for testing the operability of a vectorcardiogram machine. According to the broadest aspect of this invention, generator means are provided for generating waveforms which simulate electrical activity within the human heart along three separate axes.

In one embodiment, the device includes X waveform generator means for generating a waveform generally simulating an X-axis vectorcardiogram waveform. Y waveform generator means are provided for generating a waveform generally simulating a Y-axis vectorcardiogram waveform. Z waveform generator means are also provided for generating a waveform generally simulating a Z-axis vectorcardiogram waveform. Connector means selectively coupled to the X, Y, and Z waveform generator means are operative to supply output signals to a vectorcardiogram machine corresponding to waveforms that would ordinarily be supplied by a plurality of electrodes attached to a patient at various positions. Preferably, the connector means provides output signals which correspond to waveforms that would be generated by a patient in which the electrodes are attached at FRANK electrode positions.

According to the method of this invention, three distinct waveforms are generated by shaping and delaying a single reference waveform generally corresponding to an electrocardiogram waveform. A plurality of connectors are selectively coupled to the waveforms such that they provide output signals to the VCG machine corresponding to waveforms that would ordinarily be supplied by a plurality of electrodes attached to a live patient at various positions.

Preferably, an X waveform is generated by coupling a reference waveform, generally corresponding to an ECG waveform, to an electronic bucket brigade and delaying the output of the bucket brigade for a first time period. The Y waveform is similarly generated but its associated bucket brigade provides a delay time period different from the first time period. The Z waveform is generated by inverting the Y waveform and summing it with a reference ECG waveform. The summed waveform is inverted and coupled to a third bucket brigade which provides a third delay time period.

BRIEF DESCRIPTION OF THE DRAWINGS

These and other objects and advantages of the present invention will become apparent upon reading the following specification and by reference to the drawings in which:

FIG. 3 is a block diagram of the preferred embodiment of the electrical circuitry of the present invention;

DESCRIPTION OF THE PREFERRED EMBODIMENT

Figure 1:
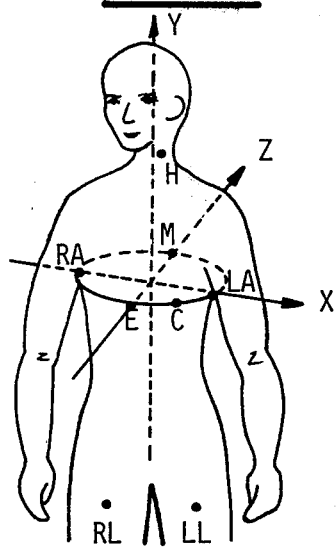
FIG. 1 is a view showing FRANK electrode positions on a patient which are used in vectorcardiography.
Figure 2:
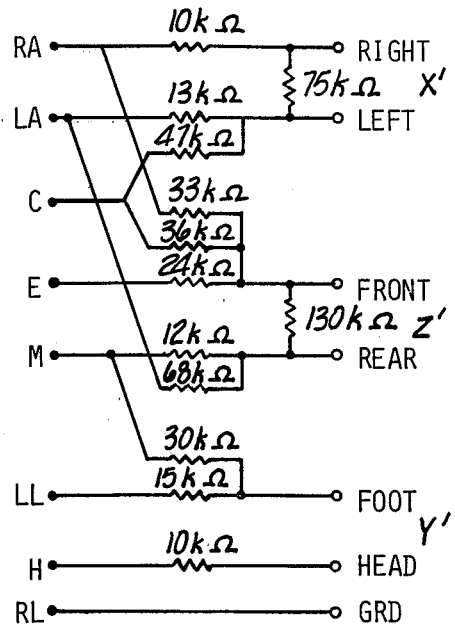
FIG. 2 is a circuit diagram showing a FRANK attenuation and compensation network.

By way of background, FIG. 1 shows typical electrode positions which are utilized in vectorcardiography. The labeled positions in FIG. 1 correspond to known FRANK electrode positions. These electrodes, labeled LA, RA, C, E, M, LL, H, and RL are coupled through a FRANK attenuation and compensation network as shown in FIG. 2 to a vectorcardiogram machine. The outputs X', Y', and Z' contain information relating to the electrical activity within the heart along the designated axes shown in FIG. 1. As is known in the art, the vectorcardiogram machine includes an X-Y oscilloscope which is used to display any two of these ECG's as a vector display or loop. The present invention is directed to simulating waveforms to be carried over the various electrodes to the vectorcardiogram machine for testing same.

FIG. 3 is a block diagram of the electrical circuitry of the present invention. The circuitry 10 includes an input 12 for receiving a simulated ECG (electrocardiographic) waveform. The simulated ECG waveform may be provided by a variety of means. A preferred means is disclosed in the above-identified U.S. Ser. No. 938,430 now U.S. Pat. No. 4,205,386), entitled "Electrocardiographic and Blood Pressure Waveform Simulator Device" which is hereby incorporated by reference. The input waveform provides a reference signal for driving basically all of the waveform generators after being buffered by buffer circuitry 14. The buffered reference waveform passes by way of amplitude and offset conditioning circuitry 16 prior to entering the chain of functional blocks making up the X and Y generators. The Y waveform generator includes an electronic bucket brigade 18 for delaying the reference input signal for a predetermined period of time as defined by the Y clock 20. The delayed signal is coupled to a Y clock noise attenuator 22 which acts to cancel the effect of the clock signals on the generated output. Additional filtering is provided by a low pass filter 24. The Y component signal is amplified by buffer circuitry 26 which includes a resistive network 28 to compensate for the DC offset of the waveform.

Similarly, the X waveform generator includes bucket brigade circuitry 30 which is driven by an X clock 32 such that the bucket brigade delays the waveform for a period which is different than the delay period for the Y waveform. The X waveform generator further includes clock noise attenuator circuitry 33, low pass filter circuitry 34, X signal buffer 36 and associated offset circuitry 38, all of which operate in a similar manner as the corresponding components in the Y waveform generator.

The Z waveform generator, however, includes a summing and inverting amplifier circuit 40 which serves to sum an inverted version of the generated Y waveform with the reference ECG waveform and invert the summed waveform after suitable offset conditioning by way of circuitry 42. Buffer 44 passes the combined signal to a Z bucket brigade 46 which is driven by Z clock 48 at a frequency sufficient to cause a third predetermined delay therein. The remainder of the Z waveform generator is similar to the X and Y generators in that it includes clock noise attenuator circuitry 50 and low pass filter 52, the offsetting and buffering functions being previously performed by circuits 40, 42, and 44 in the Z waveform generator chain.

Bias circuit 49 provides the appropriate voltage levels for driving each of the bucket brigades 18, 30, and 46.

The outputs of the X, Y, and Z generators are coupled to an amplitude adjustment circuit 54 to which output connector leads LL, H, C, RA, LA, M, E, and RL are connected. The outputs of these connector leads provide input signals to a vectorcardiogram machine corresponding to waveforms that would ordinarily be supplied by a plurality of electrodes attached to a patient at various positions. In particular, the outputs of the connectors correspond to examples of signals which would be generated by a patient in which the electrodes are connected in the FRANK electrode position shown in FIG. 1.

The FRANK attenuation and compensation network shown in FIG. 2 will modify the incoming signals somewhat to provide X', Y', and Z' waveforms to the VCG according to this known convention. However, the simulated X, Y, and Z waveforms provided by the respective generators generally correspond to waveforms which are representative of electrical activity within the human heart along the X, Y, and Z axes shown in FIG. 1. Thus, the simulator device of the present invention may be made compatible with other electrode conventions such as axial, cube, and tetrahedron electrode positions with but minor modifications.

Turning now to the details of the circuitry shown in FIG. 4, the components making up the functional blocks of FIG. 3 will be encompassed by dotted lines to aid the reader in ascertaining the correspondence therebetween. A description of the component by component interconnection in the specification will not be undertaken since the precise interconnection details are more than obvious by reference to the drawings. Instead, only the major functional components will be described.

Figure 4A:
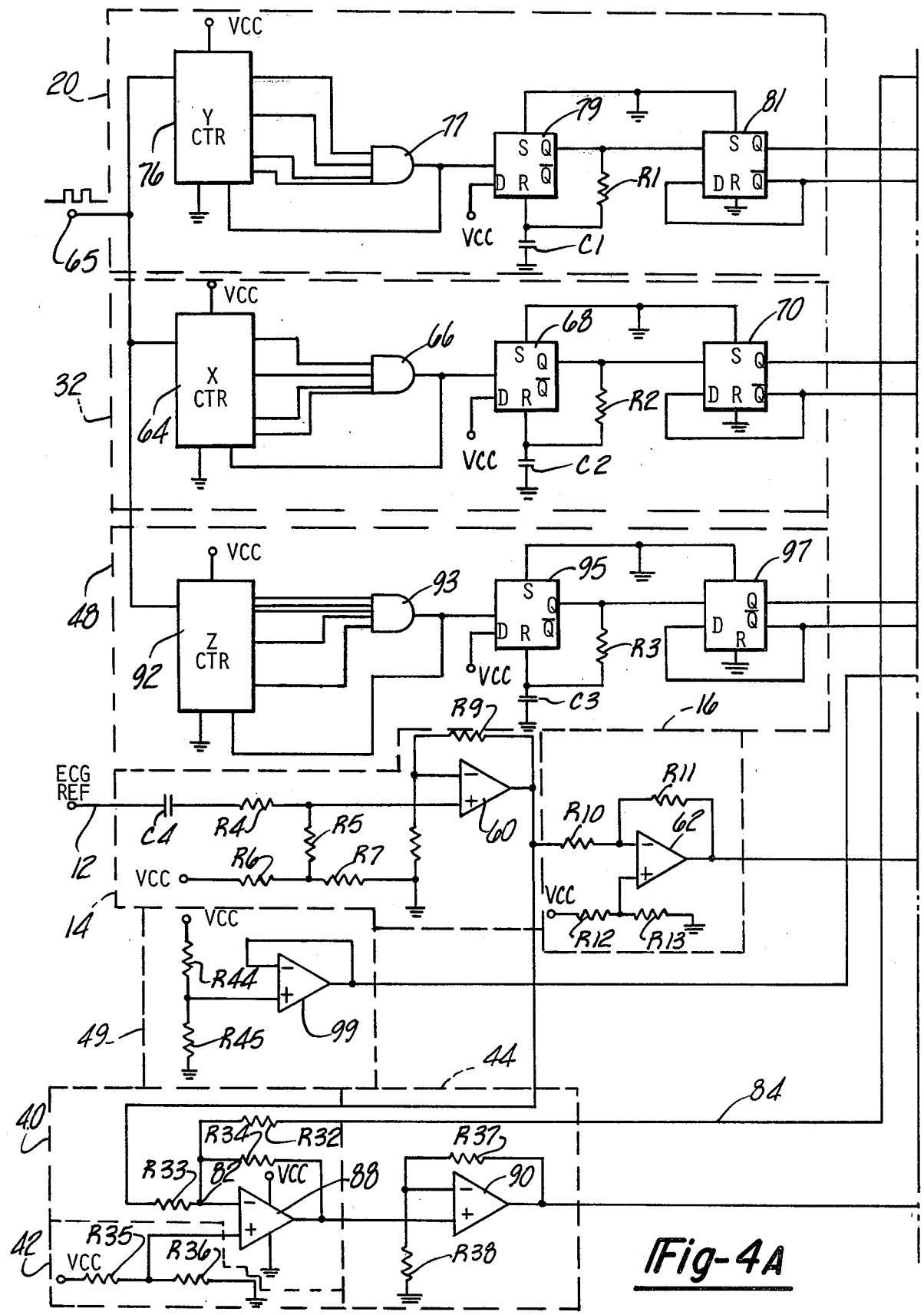
FIGS. 4 (A–B) is a schematic diagram showing the details of the circuitry shown in block diagram form in FIG. 3.

In FIG. 4A, input buffer 14 utilizes an operational amplifier 60 having its noninverting input coupled for receipt of the ECG reference waveform over input 12. Capacitor C4 and resistors R4-R9 cooperate to provide filtering and appropriate configuring of amplifier 60 to provide signal isolation.

Amplitude and offset conditioning circuitry 16 includes amplifier 62 having its inverting input coupled for receipt of the reference ECG waveform which inverts same. Resistors R12 and R13 provide an offset voltage to the noninverting input of amplifier 62. Circuitry 16 conditions the signal to provide a voltage level compatible with the particular bucket brigades 18 and 30 being utilized.

X bucket brigade 30 (FIG. 4B) is an analog delay device which accepts the output from amplifier 62 at its input and delays the generation of basically the same signal at its output for a given time period. The delay time period varies inversely with the frequency of the driving pulses from the X-clock 32 and proportionally with the number of buckets or stages in the brigade. Bucket brigade 30, in this embodiment, utilizes two clock inputs C1 and C2 and generates two output signals over lines labeled 01 and 02. X clock 32 provides two phase clock signals with a 50% duty cycle to inputs C1 and C2 of bucket brigade 30. FIG. 5 shows a timing chart of the two phase signals generated by X clock 32. These signals may be provided by a variety of known two phase clock generator circuits. In the preferred embodiment, X clock 32 uses a binary counter 64 (FIG. 4A) coupled to an externally generated master clock signal 65 of approximately 491.5 kilo-Hertz. Binary counter 64 is typical of counters known in the art and may be such as the one manufactured by National Semiconductor as component No. 4040. As is known in the art, binary counter 64 includes a plurality of output lines which are selectively activated for each incoming clock pulse to provide a coded output signal. By judicious choice of selecting particular ones of the output lines, one can develop a given clock frequency by gating these lines together as by AND gate 66. In such manner, AND gate 66 will provide output pulses at a particular frequency. The output of AND gate 66 is coupled to the input of a divide by two network comprised of cascaded flip flops 68 and 70. The flip flops 68 and 70 are coupled together in a known manner, with the Q and $\overline{Q}$ outputs of flip flop 70 providing the two phase clock signals to X bucket brigade 30 inputs C1 and C2. The frequency of these signals, in this embodiment, is about 7062 hertz.

The X bucket brigade 30, with driving clock frequencies at this level, provides a signal delay of about 35.7 milliseconds. The X bucket brigade 30 is one half of a dual 512 stage low noise BBD which, in this embodiment, is manufactured by Matsushita Electronics Corporation as component No. MN3010.

The two outputs 01 and 02 of X bucket brigade 30 are summed together at potentiometer R21. A resistive network using resistors R19 and R20 coupled to outputs 01 and 02, respectively, serve to attenuate noise created in bucket brigade 30 by the relatively high frequency clock pulses.

Additional filtering is accomplished by X low pass filter 34 which utilizes operational amplifier 72 configured as a two pole Bessel filter. Filter 34 passes signals having frequencies below 100 hertz and rejects frequencies higher than 100 hertz. Since the frequency components of the reference ECG waveform are generally at frequencies of less than 100 hertz, the waveform of interest will pass through filter 34, with spurious noise being cancelled therefrom.

The output of low pass filter 34 is coupled to the input of X signal buffer 36. Buffer 36 includes an amplifier 74 which amplifies the incoming signal according to the ratio of the feedback resistor R25 and input resistor R24 as is known in the art. Resistor divider circuitry comprised of resistors R26 and R27 coupled to the non-inverting input of amplifier 74 make up offset network 38 and serve to remove DC components of the waveform. Since the signal of interest is coupled to the inverting input of amplifier 74, the thus generated X waveform is re-inverted, i.e., having the same general orientation as the reference ECG input which was originally inverted by circuitry 16.

The Y waveform generator generally corresponds with the X waveform generator, with two notable exceptions. The Y clock 20 utilizes counter 76 whose output lines are selected in such a manner that the clock frequency ultimately generated at the output of flip flop 81 is different than that supplied by X clock 32. In this embodiment, the clock frequency generated by the Y clock 20 is about 6,607 Hertz, thus causing a delay in Y bucket brigade 18 of about 38.7 milliseconds. Another exception is that the Y signal buffer 26 amplifies the signal by a factor greater than that of the X buffer 36. It should also be noted that the output of Y low pass filter 24 includes a feedback line 84 which provides an inverted version of the Y signal to the summing and inverting amplifier 40 of the Z waveform generator.

Referring now to FIG. 4A, the feedback line 84 is coupled to a summing node 82 wherein the inverted version of the Y signal is summed with the ECG reference waveform from input buffer 14. The summed signal is coupled to the inverting input of amplifier 88. Offset circuitry 42 includes resistor divider network made up of resistors R35 and R36. The offset potential generated thereby is coupled to the non-inverting input of amplifier 88. The output of amplifier 88 is thus an inverted composite waveform made up of an inverted version of the Y waveform summed with the reference ECG waveform.

Figure 4B:
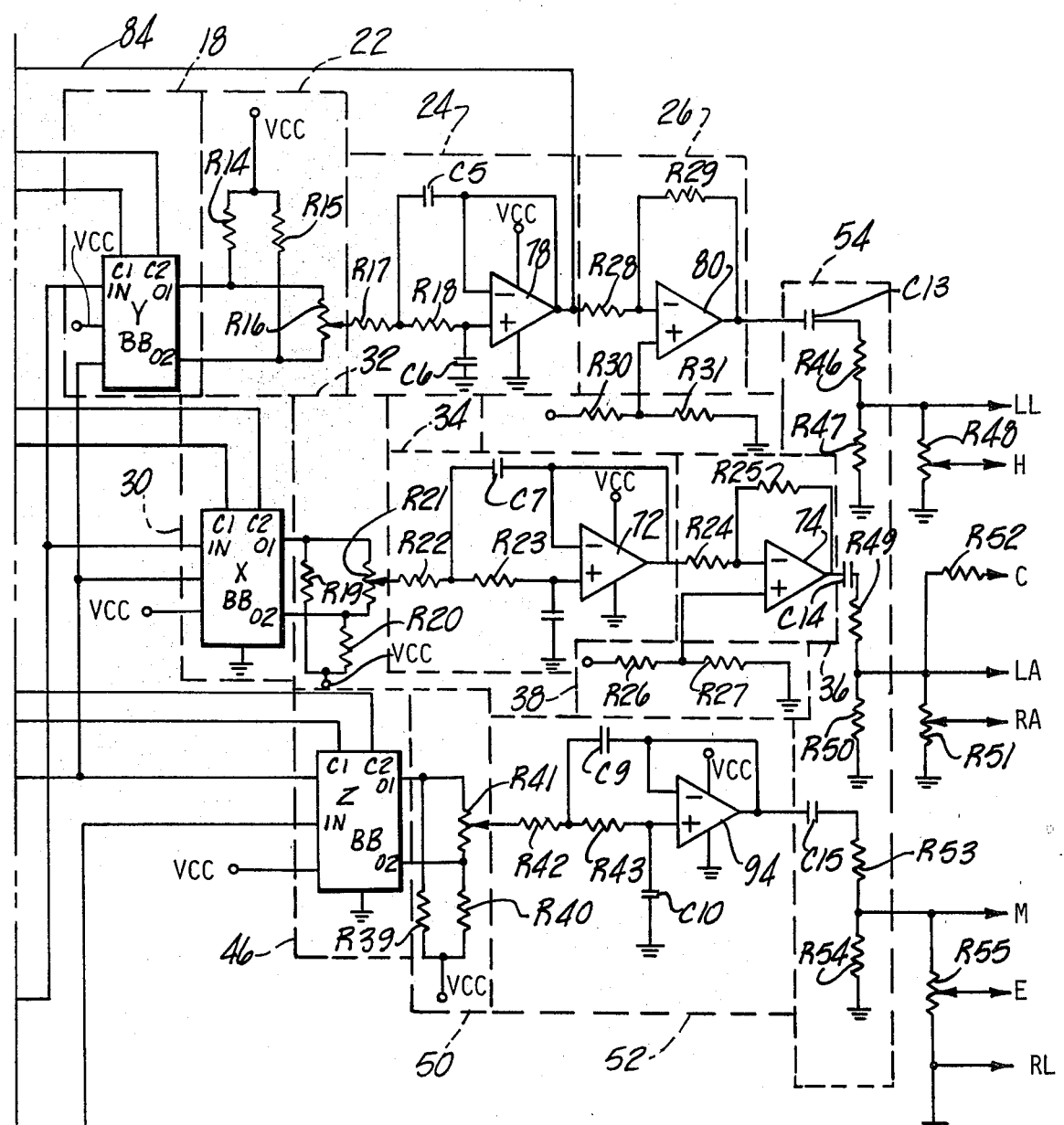
Figure 5:
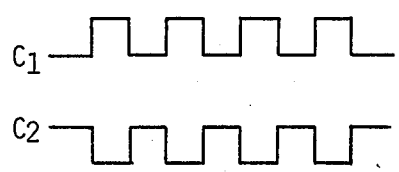
FIG. 5 is a timing chart showing clock signals utilized by the circuitry of FIG. 4.

Buffer circuitry 44 utilizes operational amplifier 90 to condition the resulting signal to an appropriate voltage level compatible with the Z bucket brigade 46 (FIG. 4B).

Z bucket brigade 46 is similar to the X bucket brigade 30 and Y bucket brigade 18 but it only includes 128 stages as compared with the 512 stages of the X and Y bucket brigades. In this particular embodiment, Z bucket brigade 46 is component number MN3006 by Matsushita Electronics Corporation. The Z clock 48 includes counter 92 (FIG. 4A) configured such that the clock frequencies to bucket brigade 46 inputs C1 and C2 are at frequencies of about 2234 hertz. At this clock frequency and given this number of stages, bucket brigade 48 provides a delay of about 28.6 milliseconds.

The Z clock noise attenuator circuitry 50 and low pass filter network 52 operate identically with their X and Y counterparts.

Figure 6:
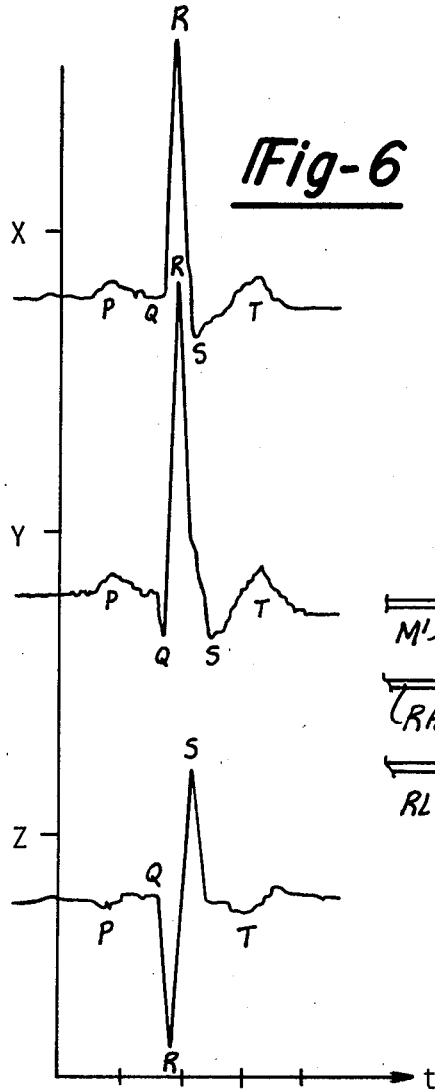
FIG. 6 is a graph showing X, Y, and Z waveforms generated according to the teachings of the present invention.

FIG. 6 shows representative signals generated by the X, Y and Z waveform generators. The X-waveform shown is that substantially generated at the output of X signal buffer 36. The X waveform is characterized by a shape generally following the contour of the reference ECG input waveform but it is delayed about 35.7 milliseconds therefrom. The Y waveform shown in FIG. 6 is substantially that provided at the output of Y buffer 26. The Y waveform generally corresponds with the X waveform but its amplitude is greater than the X amplitude by a factor of about three and it is delayed therefrom about five milliseconds. The Z waveform is characterized by two successive opposing peaks. The negative or R segment peak is derived from the R segment of the ECG reference waveform and occurs, in this embodiment, approximately seven milliseconds before the X waveform peak or R segment. The positive Z waveform peak is derived from the R segment of the Y waveform which is fed back to the summing and inverting amplifier 40. Since the Y waveform has already been delayed via bucket brigade 18, the positive peak making up the S segment of the Z waveform will be delayed from its R segment, such delay being about 35–40 milliseconds in this embodiment. The amplitude of the Z waveform is about two-thirds that of the X waveform.

The X, Y, and Z signals simulate electrical activity within the human heart along three separate axes. While the specific delays and amplitudes for these waveforms have provided a standard VCG loop for a range of normal adults, they should be considered only as specific examples and not in a limiting sense. Different amplitudes and delays will produce different loops on the VCG which may similarly be used as a calibration reference. However, in order to produce loops which are similar to those made in normal use, the X, Y and Z waveforms must meet certain criteria. The Y waveform should be delayed from the X waveform and the Z waveform should be characterized by two successive opposing major peaks corresponding to the R and S segments, respectively.

Returning now to FIG. 4B, the amplitude adjustment circuitry 54 includes capacitor-resistor networks coupled to the outputs of the X, Y, and Z waveform generators. DC blocking capacitor C13 is disposed between the output of Y signal buffer 26 and two series connected resistors R46 and R47. Likewise, the series connected network of capacitor C14 and resistors R49 and R50 are coupled to the output of X signal buffer 36. The network comprised of capacitor C15 and resistors R53 and R54 are coupled to the output of Z low pass filter 52. The pairs of resistors in each of these networks serve to provide differential outputs for further adjusting the amplitudes of the generated waveforms.

A plurality of connectors are coupled to selected outputs of the amplitude adjustment circuitry 54. The connectors labeled LL, H, C, LA, RA, M, E, and RL provide outputs for the simulator device for connecting with corresponding FRANK lead system electrodes from a vectorcardiogram (VCG) machine. The LL connector includes a lead coupled between resistors R46 and R47. The H lead is connected to the LL lead through a variable resistor device R48. The LA connector includes a lead coupled between resistors R49 and R50. The C lead is connected to the LA lead through resistor R52. The RA lead is coupled to the LA lead through a variable resistor R51. The M lead is coupled between resistors R53 and R54. The E lead is coupled to the M lead through a variable resistor R55, with the RL lead being coupled to ground.

The following table lists the component numbers and values for the referenced components which comprise the electrical circuitry of the particular embodiment just described. This table merely describes typical values and choices for such components and should not be construed in a limiting sense.

| Ref. No. | Comp. No. | Ref. No. | Value | Ref. No. | Value |
|---|---|---|---|---|---|
| 76 | 4040 | R1 | 51K | C1 | 220pf |
| 77 | 4023 | R2 | 51K | C2 | 220pf |
| 68/70 | 4013 | R3 | 51K | C3 | 220pf |
| 79/81 | 4013 | R4 | 10K | C4 | 10μf |
| 95/97 | 4013 | R5 | 100K | C5 | .047μf |
| 60 | 324 | R6 | 90.9K | C6 | .033μf |
| 62 | 324 | R7 | 25.5K | C7 | .047 |
| 74 | 324 | R8 | 10K | C8 | .033 |
| 80 | 324 | R9 | 10K | C9 | .047μf |
| 18 | 3010 | R10 | 10K | C10 | .033μf |
| 30 | 3010 | R11 | 1K | C11 | 10μf |
| 78 | OP20 | R12 | 24.3K | C12 | .22μf |
| 72 | OP20 | R13 | 26.7K | C13 | 10μf |
| 88 | 324 | R14 | 33.2K | C14 | 10μf |
| 99 | 324 | R15 | 33.2K | C15 | 10μf |
| 90 | 324 | R16 | 100K pot | | |
| 46 | 3006 | R17 | 30.1K | | |
| 94 | OP20 | R18 | 30.1K | | |
| 64 | 4040 | R19 | 33.2K | | |
| 92 | 4040 | R20 | 33.2K | | |
| | | R21 | 100K pot | | |
| | | R22 | 30.1K | | |
| | | R23 | 30.1K | | |
| | | R24 | 10K | | |
| | | R25 | 9.09K | | |
| | | R26 | 61.9K | | |
| | | R27 | 32.4K | | |
| | | R28 | 10K | | |
| | | R29 | 30.1K | | |
| | | R30 | 18.2K | | |
| | | R31 | 39.2K | | |
| | | R32 | 5.11K | | |
| | | R33 | 121K | | |
| | | R34 | 4.02K | | |
| | | R35 | 100K | | |
| | | R36 | 100K | | |
| | | R37 | 1K | | |
| | | R38 | 10K | | |
| | | R39 | 33.2K | | |
| | | R40 | 33.2K | | |
| | | R41 | 100K pot | | |
| | | R42 | 30.1K | | |
| | | R43 | 30.1K | | |
| | | R44 | 49.9K | | |
| | | R45 | 4.99K | | |
| | | R46 | 100K | | |
| | | R47 | 4020Ω | | |
| | | R48 | 100K pot | | |
| | | R49 | 100K | | |
| | | R50 | 4020Ω | | |
| | | R51 | 100K pot | | |
| | | R52 | 20K | | |
| | | R53 | 100K | | |
| | | R54 | 4020Ω | | |
| | | R55 | 100K pot | | |

Figure 7:
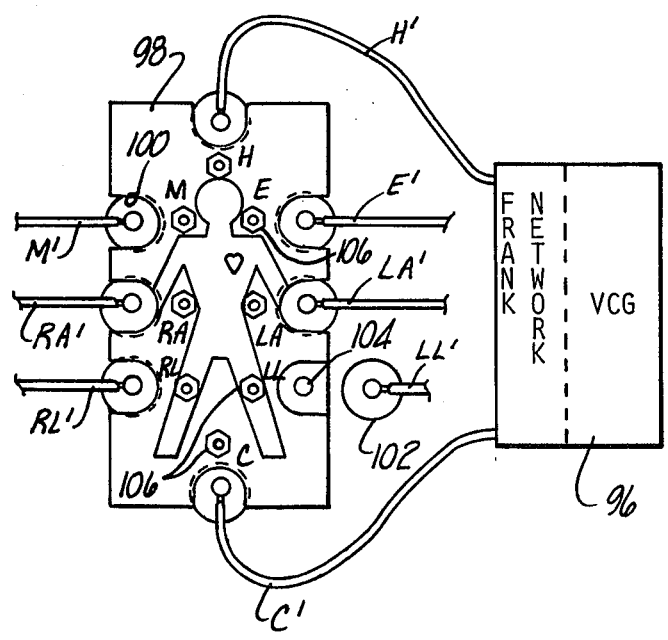
FIG. 7 is a plan view illustrating the simulator device of the present invention in use with a vectorcardiogram machine.

FIG. 7 shows one example of an interconnection system for coupling the simulated waveforms to a VCG machine 96 which includes a plurality of FRANK lead system electrodes labeled LL', H', RL', M', E', C', LA', and RA'. A housing 98 includes suitable terminals thereon for making electrical connection to the electrodes. In this embodiment, housing 98 includes slots 100 for receiving electrodes 102, with spring loaded terminals 104 making the electrical connection to electrodes 102. Posts 106 provides alternative connectors for receiving jacks utilized with disposable type electrodes. The interconnection system shown in FIG. 7 is more fully described in U.S. patent application Ser. No. 93,086, now U.S. Pat. No. 4,267,576, entitled "Interconnection System For A Biological Waveform Simulator Device" by Power et al, filed concurrently herewith and having the same assignee as the present invention. This application is hereby incorporated by reference.

In operation, the electrodes of the VCG machine 96 are coupled to corresponding connectors on device 98 which supply simulated vectorcardiographic signals for testing the operability of the VCG machine 96. Therefore, the technician can observe the output of VCG machine 96 and readily determine whether it is operating properly.

It should be understood that while this invention was described in connection with specific examples thereof, no limitation is intended thereby except as defined in the appended claims.

The embodiments of the invention in which an exclusive property or privilege is claimed are defined as follows:

1. An electronic waveform simulator for generating simulated waveforms for testing the operability of a vectorcardiogram machine, said device comprising:
   reference means for providing a reference simulated electrocardiogram waveform;
   X waveform generator means for generating a waveform simulating an X-axis vectorcardiogram waveform, said X waveform generator means including a first electronic bucket brigade having an input coupled for receipt of said reference waveform, operative to delay the generation of said reference waveform at an output of the first electronic bucket brigade for a first given time period;
   Y waveform generator means for generating a waveform generally simulating a Y-axis vectorcardiogram waveform and having an input coupled for receipt of said reference waveform;
   Z waveform generator means for generating a waveform generally simulating a Z-axis vectorcardiogram waveform and having an input coupled for receipt of said reference waveform; and
   connector means selectively coupled to the X, Y and Z waveform generator means, operative to supply output signals to a vectorcardiogram machine corresponding to waveforms ordinarily supplied by a plurality of electrodes attached to a live patient at various positions.

2. The device of claim 1 wherein said X waveform generator means further comprises:
   X clock means for providing clock signals at a first frequency for driving said first bucket brigade.

3. The device of claim 2 wherein said X clock means provide clock signals for driving the said first bucket brigade at a frequency to cause a delay therein of about 35.7 milliseconds.

4. The device of claim 3 which further comprises:
   first clock noise attenuator means coupled to the output of said first bucket brigade, operative to attenuate electrical noise created in the first bucket brigade by said clock signals.

5. The device of claim 4 wherein said X waveform generator means further comprises:
   a first low pass filter means coupled to the output of said first clock noise attenuator means, operative to pass signals having frequencies less than 100 Hertz and removing signals having frequencies above 100 Hertz.

6. The device of claim 5 wherein said X waveform generator means further includes first buffer amplifier means including a first amplifier for amplifying the signal from the first low pass filter means by a predetermined gain factor; and
   first offsetting means coupled to said first amplifier for offsetting DC components of the incoming signal to the first amplifier.

7. The device of claim 6 wherein said Y waveform generator further comprises:
   a second electronic bucket brigade having an input coupled for receipt of said reference waveform, operative to delay the generation of said reference waveform at an output of said second electronic bucket brigade for a second given time period different from the first given time period.

8. The device of claim 7 wherein said Y waveform generator means further comprises:
   Y clock means for providing clock signals at a second clock frequency for driving said second bucket brigade.

9. The device of claim 8 wherein said Y clock means provides clock signals at a frequency for causing a delay time period in said second bucket brigade of about 38.7 milliseconds.

10. The device of claim 9 wherein said Y waveform generator means further comprises second clock noise attenuator means, operative to attenuate electrical noise in said second bucket brigade created by said Y clock signals.

11. The device of claim 10 wherein said Y waveform generator means further comprises:
    second low pass filter means coupled to the output of said second clock noise attenuator means, operative to pass signals having frequencies less than 100 Hertz and cancelling signals having frequencies above 100 Hertz.

12. The device of claim 11 wherein said Y waveform generator means further comprises:
    second buffer amplifier means including a second amplifier for amplifying the output of said second low pass filter means by a gain factor greater than the gain factor supplied by said first buffer amplifier means; and second offsetting means coupled to said second amplifier for offsetting DC components of the incoming signal to the second amplifier.

13. The device of claim 12 wherein said Z waveform generator means comprises:
    summing means for summing the reference waveform with a waveform generally corresponding to an inverted form of the waveform generated by said Y waveform generator means;
    inverter means for inverting said summed waveform; and
    third delay means operative to delay the generation of said summed waveform at an output of the third delay means for a third given time period.

14. The device of claim 13 wherein said Z waveform generator means further comprises a third electronic bucket brigade.

15. The device of claim 14 wherein said Z waveform generator means further comprises Z clock means for providing clock signals at a third clock frequency for driving said third bucket brigade so as to cause a delay period therein of about 28.6 milliseconds.

16. The device of claim 15 wherein said Z waveform generator means further comprises:
    third clock noise attenuator means, operative to attenuate electrical noise created in said third bucket brigade by said clock signals.

17. The device of claim 16 wherein said Z waveform generator means further comprises third low pass filter means coupled to the output of said third clock noise attenuator means, operative to pass signals having frequencies below about 100 Hertz and cancel signals having frequencies above about 100 Hertz.

18. The device of claim 1 which further comprises:
    amplitude adjustment means disposed between the outputs of said X, Y, and Z waveform generator means and said connectors, operative to selectively adjust the amplitude of said waveforms.

19. The device of claim 18 wherein said amplitude adjustment means comprises:
    X, Y, and Z amplitude adjustment networks coupled to the outputs of said X, Y, and Z waveform generator means, respectively; each network comprising a series connected capacitor and two series connected resistors.

20. The device of claim 19 wherein said connector means comprises a plurality of electrically conductive leads corresponding to LL, H, C, LA, RA, M, E, and RL FRANK system electrodes; said LL lead being coupled between the two resistors of the Y amplification adjustment network; the H lead being connected to the LL lead through a variable resistor device; the LA lead being coupled between the two resistors of the X amplitude adjustment network; the C lead being connected to the LA lead through a resistor; the RA lead being coupled to the LA lead through a variable resistor device; the M lead being connected between the two resistors of the Z amplitude adjustment network; the E lead being connected to the M lead through a variable resistor device; and the RL lead being connected to ground.

21. A method of providing simulated biological waveforms for testing the operability of a vectorcardiogram machine, said method comprising:
    generating a first distinct waveform simulating electrical activity within the human heart along a first axis, said waveform being generated by delaying a single reference waveform generally corresponding to an electrocardiogram waveform by a first time period;

generating a second distinct waveform simulating electrical activity within the human heart along a second axis, said waveform being generated by delaying the reference waveform by a second time period greater than the first time period;

generating a third distinct waveform simulating electrical activity within the human heart along a third axis, said third waveform being generated by summing the reference waveform with an inverted version of the second waveform and inverting the summed composite waveform; and selectively coupling a plurality of connectors to said first, second and third generated waveforms to provide output signals to a vectorcardiogram machine corresponding to waveforms ordinarily supplied by electrodes attached to a live patient at various positions.

22. A method of generating simulated waveforms for testing the operability of a vectorcardiogram machine, said method comprising:

generating an X waveform by coupling a reference waveform generally corresponding to an electrocardiogram waveform to a first electronic bucket brigade, and delaying the output of the first bucket brigade for a first time period;

generating a Y waveform by coupling a reference waveform generally corresponding to an electrocardiogram waveform to a second bucket brigade, and delaying the output of the second bucket brigade for a second time period;

generating a Z waveform by inverting a previously generated Y waveform and summing it with a reference waveform generally corresponding to an electrocardiogram waveform, inverting the summed waveform, coupling the summed waveform to a third bucket brigade, and then delaying the output of the third bucket brigade for a third time period; and selectively coupling the X, Y, and Z waveforms to a plurality of connectors for providing output signals to a vectorcardiogram machine corresponding to waveforms that would ordinarily be supplied by a plurality of electrodes attached to a patient at a variety of selected positions.

* * * * *